(12) United States Patent
Säll et al.

(10) Patent No.: US 10,702,657 B2
(45) Date of Patent: Jul. 7, 2020

(54) INFORMATION PROVIDER ASSEMBLY AND MEDICAMENT DELIVERY DEVICE COMPRISING THE SAME

(71) Applicant: SHL MEDICAL AG, Zug (CH)

(72) Inventors: Daniel Säll, Segeltorp (SE); Rasmus Renstad, Stockholm (SE); Nikolaj Hautaviita, Bro (SE)

(73) Assignee: SHL MEDICAL AG, Zug (CH)

( * ) Notice: Subject to any disclaimer, the term of this patent is extended or adjusted under 35 U.S.C. 154(b) by 238 days.

(21) Appl. No.: 15/563,041

(22) PCT Filed: Mar. 9, 2016

(86) PCT No.: PCT/EP2016/054989
§ 371 (c)(1),
(2) Date: Sep. 29, 2017

(87) PCT Pub. No.: WO2016/155997
PCT Pub. Date: Oct. 6, 2016

(65) Prior Publication Data
US 2018/0064879 A1 Mar. 8, 2018

(30) Foreign Application Priority Data

Mar. 30, 2015 (EP) .................................... 15161685

(51) Int. Cl.
*A61M 5/315* (2006.01)
*G06F 19/00* (2018.01)

(52) U.S. Cl.
CPC ..... *A61M 5/31525* (2013.01); *G06F 19/3468* (2013.01); *A61M 2205/583* (2013.01); *A61M 2209/086* (2013.01)

(58) Field of Classification Search
CPC ...... A61M 5/513525; A61M 2205/583; A61M 2205/52; A61M 2205/3306; A61M 2209/086
See application file for complete search history.

(56) References Cited

U.S. PATENT DOCUMENTS 5,536,249 A 7/1996 Castellano et al.
5,782,814 A * 7/1998 Brown ................ A61M 5/1685
604/207

(Continued)

FOREIGN PATENT DOCUMENTS

WO 2013050585 A1 4/2013

*Primary Examiner* — Laura A Bouchelle
(74) *Attorney, Agent, or Firm* — McDonnell Boehnen Hulbert & Berghoff LLP

(57) ABSTRACT

The present invention relates to an information provider assembly to be used with a medicament delivery device for providing status information of the medicament delivery device, which medicament delivery device is provided with a medicament dose setting mechanism, the information provider assembly comprising a housing designed to be releasibly connectable to said medicament delivery device, the information provider assembly further comprising a measuring unit capable of measuring the position of a measuring surface on said medicament delivery device, which measuring surface is moved as the medicament dose setting mechanism is operated. The invention is characterized in that the measuring unit is capable of measuring the measuring surface before and after operation of the dose setting mechanism, when said housing is connected, wherein the difference in positioning of the first reference points before and after operation of the dose setting mechanism constitutes information regarding set and delivered dose of medicament.

15 Claims, 6 Drawing Sheets

(56) References Cited

U.S. PATENT DOCUMENTS 8,556,867 B2 * 10/2013 Krulevitch .............. A61M 5/24
                                                      604/223
2003/0233069 A1   12/2003 Gillespie, Jr. et al.

* cited by examiner

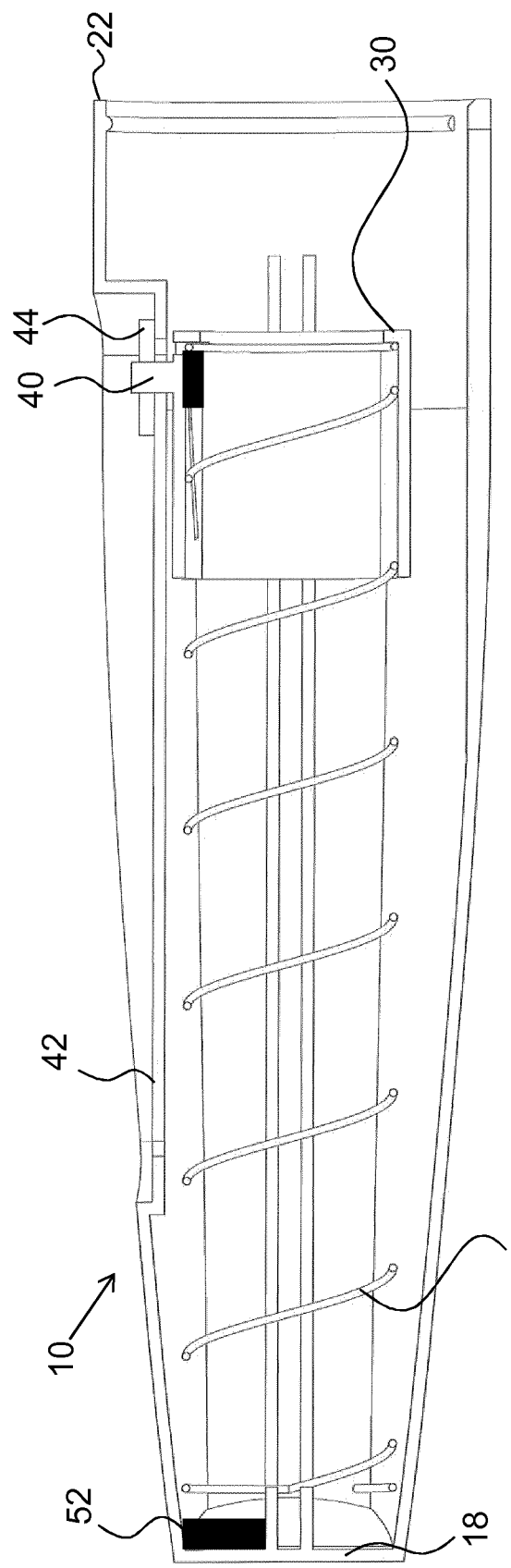
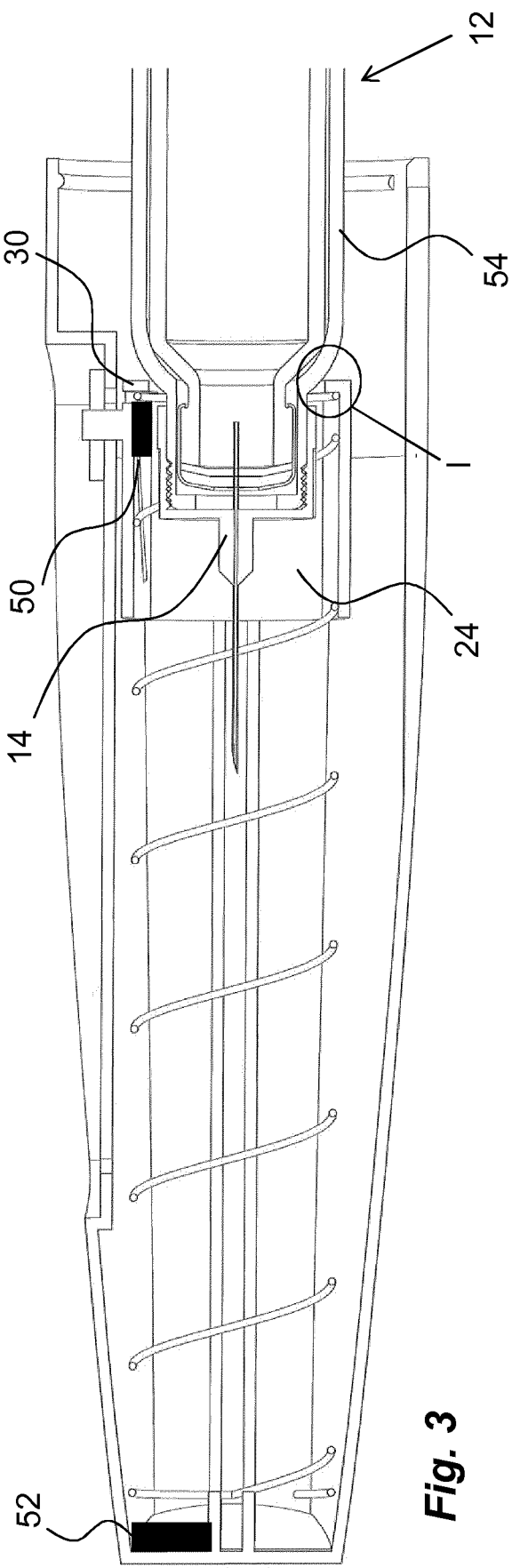
Fig. 2
Fig. 3

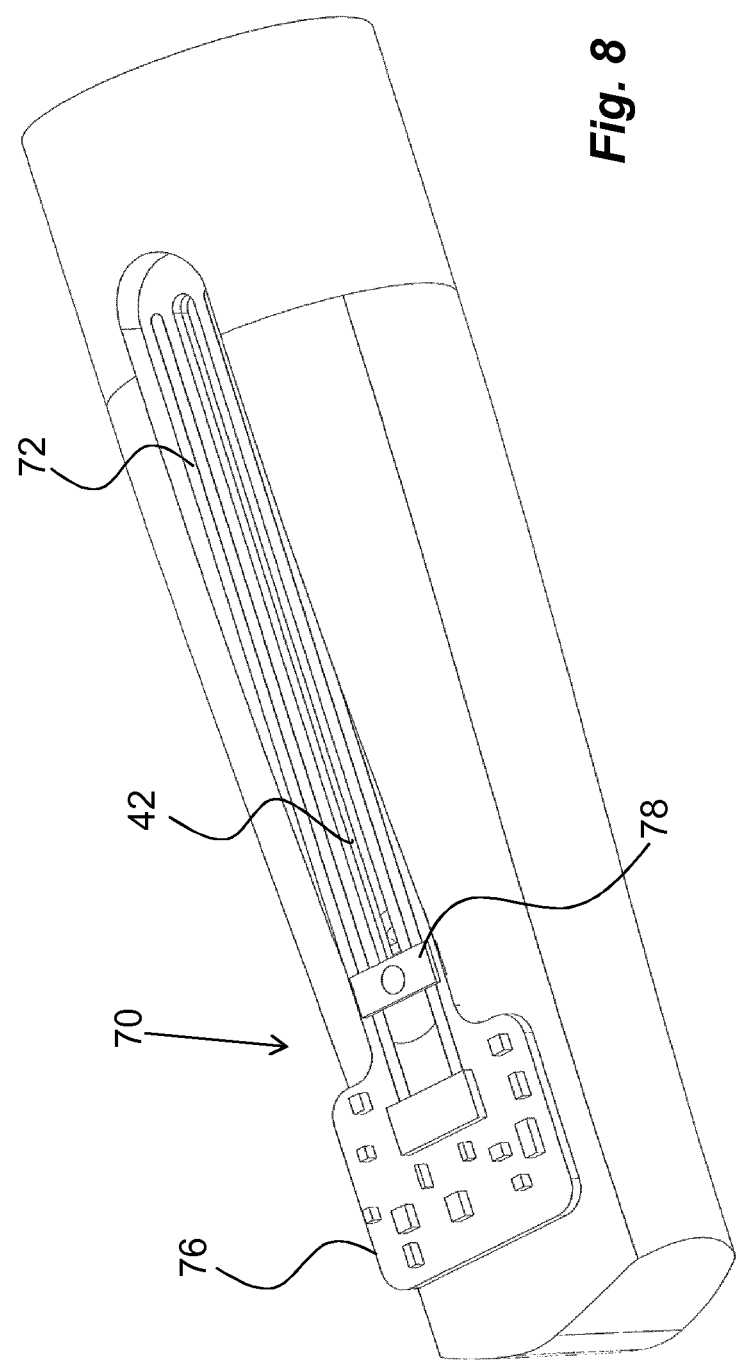

INFORMATION PROVIDER ASSEMBLY AND MEDICAMENT DELIVERY DEVICE COMPRISING THE SAME

CROSS REFERENCE TO RELATED APPLICATIONS

The present application is a U.S. National Phase Application pursuant to 35 U.S.C. § 371 of International Application No. PCT/EP2016/054989 filed Mar. 9, 2016, which claims priority to European Patent Application No. 15161685.1 filed Mar. 30, 2015. The entire disclosure contents of these applications are herewith incorporated by reference into the present application.

TECHNICAL AREA

The present invention relates to an information provider assembly and in particular an information provider assembly that is to be used with a medicament delivery device in order to retrieve information regarding status of the medicament delivery device.

BACKGROUND OF INVENTION

There is an increased demand for obtaining information from, and for monitoring the use of, medicament delivery devices that are handled by non-professionals, e.g. devices handled by the users themselves.

One important reason for the monitoring demands is that many physicians want to have information regarding how the patients are handling the medication based on the prescribed treatment schemes. Since many users do not meet their physicians very often, it may be difficult to have a good overview of how the patients are handling their treatments. Also, since some drugs are quite expensive, it is important that the drugs are used properly by the rightful user. Further, many drugs do not require so frequent dosing, whereby there is an increased risk that the user forgets to take the medication.

Some devices have been developed that can monitor the medicament delivery devices in order to retrieve information regarding the status of the devices. The document U.S. Pat. No. 5,536,249 discloses an injector having a microprocessor. The device is further arranged with a dose setting knob that in turn is connected to an electronic counter, which in turn is connected to the microprocessor for providing information regarding the set dose. When then a start button is activated, the microprocessor stores relevant information regarding the injection, such as the time, the date and the amount of medication injected by the user. The device then comprises a data I/O port so that information stored in the device may be uploaded to a computer, preferably at the physicist.

Document WO 2013/050535 discloses a system for determining positions of elements and in particular a plunger rod movable in a medicament delivery device. According to one embodiment a protective cap is used for measuring the positions of a plunger rod before and after administration of a dose of medicament. The positions of the plunger rod are measured by a measuring unit comprising 3D magnetrons arranged on the medicament delivery device. Further supporting electronics components including magnetic data capture are arranged in the measuring unit. Electrical connectors are arranged to transmit data from the measuring unit to the protective cap as the latter is connected to the medicament delivery device. Communication means may further be provided allowing wired or wireless transfer of data to and from a PC or a smartphone.

BRIEF DESCRIPTION OF INVENTION

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present invention is to remedy the drawbacks of the state of the art devices. This aim is obtained by a medicament delivery device according to the features of the independent patent claim. Preferable embodiments of the invention form the subject of the dependent patent claims.

According to a main aspect, it comprises an information provider assembly to be used with a medicament delivery device for providing status information of the medicament delivery device, where the medicament delivery device is provided with a medicament dose setting mechanism such that a user may set a requested dose of medicament to be delivered.

The information provider assembly may preferably comprise a housing designed to be releasibly connectable to said medicament delivery device such that the information provider is attached before use and then removed during delivery of a dose of medicament, after which the housing is again connected.

The information provider assembly may further comprise a measuring unit arranged inside the housing and capable of measuring the position of a measuring surface on the medicament delivery device. The medicament delivery device is designed such that the measuring surface is moved as the medicament dose setting mechanism is operated.

In this respect, the measuring unit is capable of measuring the measuring surface before and after operation of the dose setting mechanism when the housing is connected, wherein the difference in positioning of the measuring surface before and after operation constitutes information regarding set and delivered dose of medicament. With this information regarding the two positions, it is easy to derive information regarding for instance size of the set dose and delivered dose. Further, this information could be added to a time stamp in order to obtain time and date information when the medicament delivery device was used.

Preferably the information provider assembly further comprises a first contact surface arranged to come in contact with the measuring surface. By using a mechanical contact surface, a positive and stable measuring function is obtained. In that respect, the measuring unit may comprise a movable contact element, which contact element comprises the first contact surface.

According to another aspect, the information provider may further comprise a second contact surface arranged on the housing and designed to come in contact with a reference surface fixed on the medicament delivery device. With a fixed reference surface, it is ascertained that the mutual positions of the information provider assembly and the medicament delivery device are repeated each time of connection.

According to one feasible aspect, the measuring unit may comprise a spring force element arranged to urge the contact element to a start contact position with the medicament delivery device. Again consistent contact positions are obtained with the solution.

According to another aspect, the measuring unit may be operably arranged to measure the distance that the contact element is moved from the start contact position to the position where the second contact surface is in contact with the reference point.

Preferably the measuring unit may further comprise comparing elements capable of comparing the difference in distance that said contact element has moved before and after operation of the dose setting mechanism, which difference in distance constitutes information regarding set and injected dose.

According to one feasible solution, the measuring unit may comprise a rotary encoder operably arranged to rotate when said contact element is moved. In this respect, the rotary encoder may operate with mechanical, optical, magnetic, resistive, audible or capacitive principles.

According to an alternative, the measuring unit may comprise a linear encoder operably arranged to move linearly when said contact element is moved. In this respect, the linear encoder may operate with the same principles as the rotary encoder.

The information provider assembly may preferably further comprise a communication unit, operably arranged to communicate information obtained from said measuring unit. With a communication unit, information obtained from the measuring unit may be transferred to external information handling units, such as external databases for further processing of the information.

According to one aspect, the communication unit may comprise I/O interfaces. In addition or as an alternative the communication unit may comprise a wireless communication circuit and in this respect the wireless communication circuit may be designed to communicate via near range communication technologies, cellular radio communication networks and/or local area networks. Finally, preferably the information provider assembly is arranged as a protective cap.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 2-3 are cross-sectional views of the information provider assembly of FIG. 1, FIG. 8 is a third embodiment of an information provider assembly.

DETAILED DESCRIPTION OF THE INVENTION

The present invention relates to an information provider assembly that a dose has been set and delivered by a medicament delivery device. In this context it is to be understood that the medicament delivery device is arranged with a dose setting mechanism that the user operates before a dose delivery operation.

In one embodiment shown, the information provider assembly is a cap 10 that is intended to be releasibly attachable to a medicament delivery device 12, FIG. 3, and preferably covering a proximal part of the medicament delivery device where a dose delivery member 14 is arranged, such as an injection needle. The cap then acts as a protective cap, preventing injuries by the injection needle.

Figure 1:
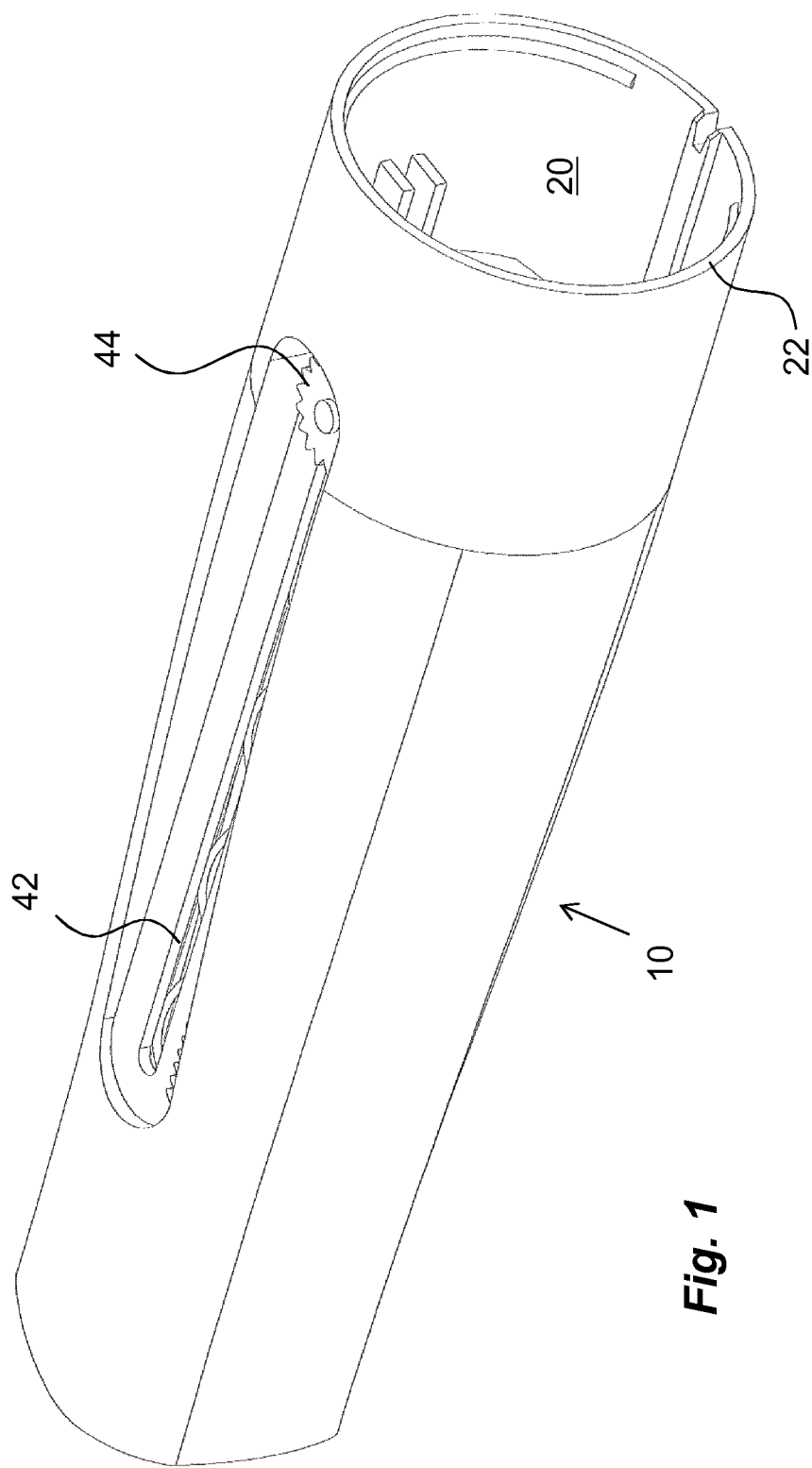
FIG. 1 shows a perspective view of a first embodiment of an information provider assembly.
Figure 4:
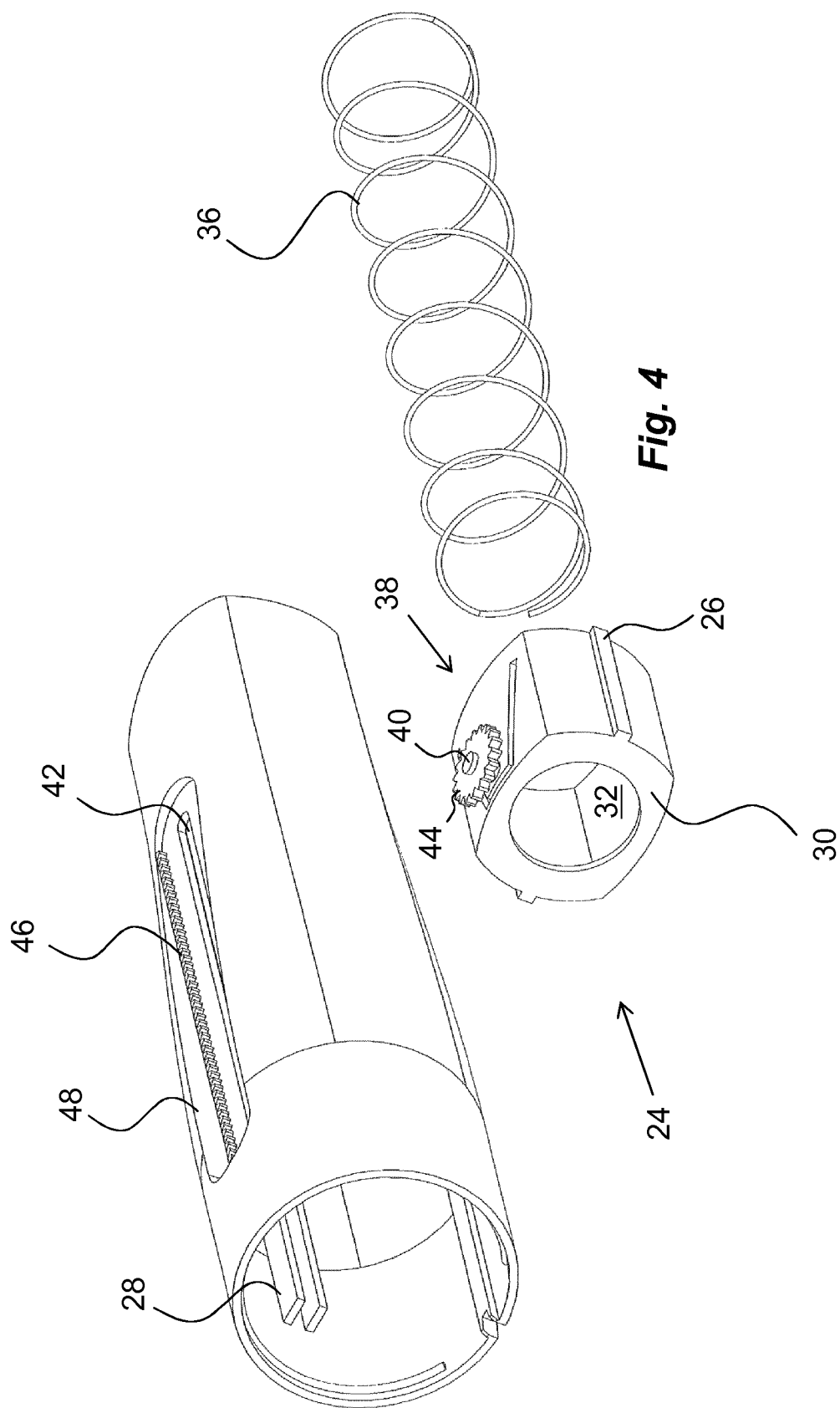
FIG. 4 is an exploded view of the information provider assembly of FIG. 1, FIGS. 5 and 6 show cross-sectional functional views.

According to the present invention, the cap is provided with a number of features and functions. As seen in FIGS. 1-3, the cap 10 has a generally tubular housing 16 with a proximal end wall 18 a distally directed passage 20 and a distally directed end surface 22. Inside the housing 16, a measuring unit 38 is arranged. The measuring unit comprises a collet 24 that is arranged movable in the longitudinal direction. In that respect, the collet 24 is arranged with longitudinally extending ridges 26 on outer side surfaces, which ridges 26 it into longitudinally extending guide ledges 28 on inner surfaces of the housing 16.

The distally directed wall 30 of the collet 24 is arranged with a passage 32, having a diameter somewhat larger than the diameter of an attachment part 34 of the injection needle 14. Further a spring 36 is arranged between a proximally directed surface of the collet 24 and a distally directed surface of the end wall 18 of the housing 16, FIG. 3, urging the collet 24 in the distal direction inside the housing.

As seen in the embodiment shown in FIG. 2, the measuring unit 38 further comprises a shaft 40 arranged rotatable on an upper surface of the collet, which shaft 40 is positioned in a longitudinally extending slit 42 in the housing 16. The upper end of the shaft 40 is arranged a cog-wheel 44, which cog-wheel 44 is in engagement with a toothed rack 46 on a longitudinally extending side wall 48 of a recess in the housing 16 of the cap. The lower end of the shaft 40 is attached to a rotary encoder 50 arranged in the collet 24 and the rotary encoder is electrically connected to an electronics unit 52. The rotary encoder 50 is arranged to provide information regarding the position of the collet 24, which data will be processed in the electronics unit 52, as will be explained. In the embodiment shown, the electronics unit is placed in the housing of the information provider, but may also be placed in the collet in order to reduce the wiring between the encoder and the electronics unit.

Figure 5:
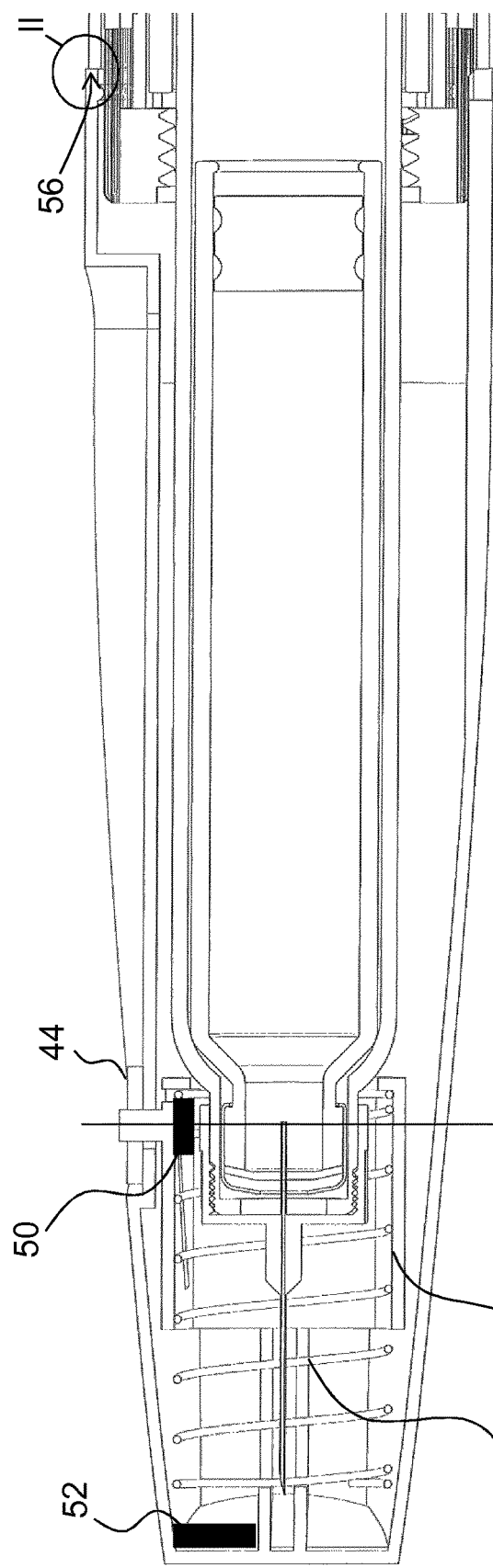

The medicament delivery device that the cap shown in the drawings is intended to be used with becomes shorter each time a dose is set. Initially, before attachment to a medicament delivery device, the collet is in a distal end position, pushed there by the force of the spring as seen in FIG. 2. When the medicament delivery device is assembled before delivery to a user, the cap is attached to a proximal housing part 54 of the medicament delivery device 12 and as seen in FIG. 3, the collet 24 comes in contact with a neck area of the proximal housing part 54 with its distally directed wall 30, constituting a first contact surface as seen in circle I of FIG. 3. This position of the collet when establishing a first contact will be referred to as the start contact position. As seen, the injection needle 14 is positioned inside the passage 32 of the collet 24. The collet 24 is moved in the proximal direction in relation to the housing 16 of the cap due to the contact with the proximal housing part 54 until the cap with its distal end surface 22 abuts against a fixed reference surface 56 of the medicament delivery device, where the distal end surface 22 constitutes a second contact surface as seen in circle II of FIG. 5.

The movement of the collet 24 from the start contact position to the capped position is registered by the measuring unit 38 in that the cog wheel 44 will rotate because of the engagement with the toothed rack 48 and because of the relative movement of the collet 24 and the housing. The rotation of the cog wheel 44 in turn causes the rotary encoder 50 to rotate a number of turns. The rotary encoder 50 is then provided with suitable means for registering the number of turns and to convert these to a distance that the collet 24 has travelled. This distance constitutes an initial value for a full and unused medicament container.

There are a number of ways that the rotary encoder 50 may keep track of the number of turns it has rotated during the movement of the collet 24. An "absolute" encoder maintains position information when power is removed from the system. The position of the encoder is available immediately on applying power. The relationship between the encoder value and the physical position of the controlled machinery is set at assembly; the system does not need to return to a calibration point to maintain position accuracy. An absolute encoder may have multiple code rings with various binary weightings which provide a data word representing the absolute position of the encoder within one revolution. This type of encoder is often referred to as a parallel absolute encoder. Digital absolute encoders produce unique digital code for each distinct angle of the shaft. There are a number of principles that absolute encoders may utilize; mechanical, optical, magnetic and capacitive.

The absolute encoders may further be so called multi-turn encoders that are capable of detecting and storing more than one revolution. These multi-turn encoders are of different types that can store the absolute positions. For instance the encoder may be battery-powered for retaining counts across power cycles, wherein the electronics unit 52 may comprise e.g. a button cell. They may also be geared in that a train of gears is used for mechanically storing the number of revolutions, where the position of each gear is detected as described above. A recent development is to use energy harvesting to generate energy from the moving shaft of the rotary encoder such as using a so called Wiegand sensor.

As an alternative, "incremental" rotary encoders may be used. An incremental encoder accurately records changes in position, but does not have a fixed relation between encoder state and physical position when activated. Devices controlled by incremental encoders may have to be positioned at a fixed reference point to initialize the position measurement. An incremental encoder functions by providing an A and a B pulse output that provide no usable count information in their own right. Rather, the counting is done in external electronics. The point where the counting begins depends on the counter in the external electronics and not on the position of the encoder. To provide useful position information, the encoder position must be referenced to the device to which it is attached, generally using an index pulse. The distinguishing feature of the incremental encoder is that it reports an incremental change in position of the encoder to the counting electronics.

When the user is to administer a dose of medicament, the cap 10 is removed. This causes the collet 24 to move to its most distal position by the force of the spring, FIG. 2. The medicament delivery device is handled such as to set a dose quantity to be delivered. The design of the medicament delivery device is such that a proximal housing part and a distal housing part are operated such during setting of a dose that the measuring surface and the reference surface are moved closer to each other, where one non-limiting design could be that the device becomes shorter when a dose is set. It is however possible that the surfaces are being moved closer to each other but that the medicament delivery device as such retains its length or even that the device as such becomes longer.

Figure 6:
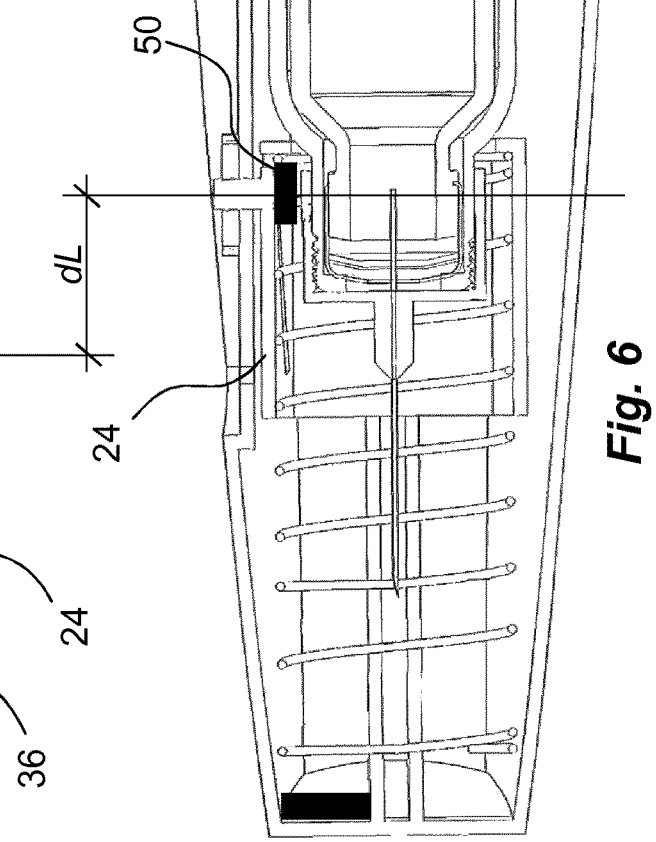

The user then performs a penetration operation of the medicament delivery member, and subsequently performs an injection operation. When completed, the medicament delivery device may be removed from the dose delivery site. Now the cap 10 is again attached to the proximal end of the medicament delivery device 12. The first contact surface of the collet 24 comes in contact with the measuring surface of the proximal end of the proximal housing part 54, FIG. 3, and is moved within the housing of the cap in the proximal direction and as described above, the rotary encoder will register the number of turns the cog-wheel will rotate and convert this to a distance travelled by the collet until the distally directed second contact surface 22 of the cap 10 will come in contact with the fixed reference surface 56 of the medicament delivery device, FIG. 6. Since the measuring surface and the reference surface have moved closer to each other, the distance that the collet now has moved is shorter than the initial distance as seen in FIG. 6 when compared to FIG. 5. The different distances that the collet has moved before and after setting and delivery of dose may be compared by the electronics 52, providing a difference in distance dL that corresponds to the dose delivered. The difference in distance may easily be converted to a volume by the electronics 52. Thus, each time a dose is to be delivered, the cap 10 is removed, the dose is set whereby the measuring surface and the reference surface move closer to each other, the injection is performed and the cap is recapped, providing an information that the dose has been delivered.

The electronics unit 52 may comprise a number of elements and functions depending on the application. For instance it may comprise a processor capable of processing program code for performing different tasks. Storage memory elements are further comprised, where program code is stored as well as information retained from the encoders for instance. The electronics unit is further connected to a user communication circuit comprising appropriate communication mechanisms such as visual information provider such as lights, displays and combinations thereof. Also audio generating mechanisms could be provided, such as speakers. Apart from providing and handling the dose delivery information, the electronics unit 52 may preferably be arranged with further functions such as time stamp function such that the time and date that a dose has been delivered is monitored and stored. The electronics unit may further be provided with an NFC-tag for deriving further information such as temperature. NFC-tags are commonly provided with a temperature sensor that is built into the NFC-chip. This may be an advantage because then the temperature of a medicament delivery device and/or a medicament container may be monitored and logged for instance during transport. This might be important for a number of drugs that are temperature sensitive, whereby it can be ensured that the quality of the drug has not been affected by temperature variations outside approved ranges. Also, the temperature sensor could be used to provide information when a drug has reached a target temperature for delivery. The information is then communicated to the smart device, where the latter provides handling and temperature information to the user.

In that respect, the communication mechanisms may be utilized such that e.g. LED's of different colour, or one LED that can change colour, may be used. The LED's are then connected to the NFC-tag such that when the temperature sensor senses a certain temperature, a certain colour is lit. When the temperature changes above or below a threshold, another colour is lit. For example, if the temperature of a drug is above or below a permissible drug delivery temperature range, then one colour is lit, e.g. a red light, indicating that the drug cannot be used yet. When then the temperature reaches the permissible range, e.g. room temperature, then the light is changed to e.g. green, indicating that the drug now may be used.

According to a further feature of the present invention, the electronics unit 52 comprises a communication unit. This communication unit is capable of transmitting the information obtained by the information provider assembly regarding the doses set and delivered as detected by the information provider assembly. The communication unit may be designed in many ways for providing the information to external sources. For instance, the information provider assembly may be arranged with a connection, to which a transmission cable may be attached.

The communication unit may further be arranged with wireless communication technologies. These communication technologies may comprise near range communication technology such as RFID, NFC or the like, as well as Bluetooth, Ant, Zigbee, just to mention a few. If for instance NFC technology is used, then a mobile device being NFC-enabled may derive the position data from the information provider assembly. The mobile device may then either be capable of handling the data, such as e.g. calculating the dose volume and registering the date of the occurrence of the medicament delivery device, or may in turn transmit the data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the communication unit as such. Then the communication unit may communicate directly with external data storage sources, data handling centres etc. via the communication networks. The data may preferably be accessible to a physician or the like skilled person that is responsible for the treatment of the user of the medicament delivery device and who might have put together a treatment scheme. This retrieved data may then be evaluated to derive information such as adherence, and the lack of which may lead to measures from the physician.

These measures may be that information is transmitted back to the electronics via the communication circuits, which information retrieved by the information provider assembly may be communicated to the user via a user communication circuit, and in particular if the user has deviated from the prescribed treatment scheme. The user may in that respect also be informed what measures that need to be taken in order to remedy the deviation. The information may be presented visually or audibly via the user communication circuit. One practical user information that could be transmitted to the user communication circuit and presented to the user is a reminder message. Thus, based on the treatment scheme that has been set by the physician of the patient, the user communication circuit may alert when a dose of medicament is to be taken.

The communication unit may further be arranged with a circuit that is arranged to transmit a signal or a short data message at periodic intervals to an external data information handling centre that preferably is the same as for the monitoring data. This data is to inform that the device is operational and ready to be used. Thus, if no dose delivery information is received from the device but an operation signal is received, then this is a clear indication that the patient does not comply with the treatment scheme. If no operation signal was used, then it is difficult, when monitoring the patient, to know if the device is non-operational or if the patient does not comply.

Figure 7:
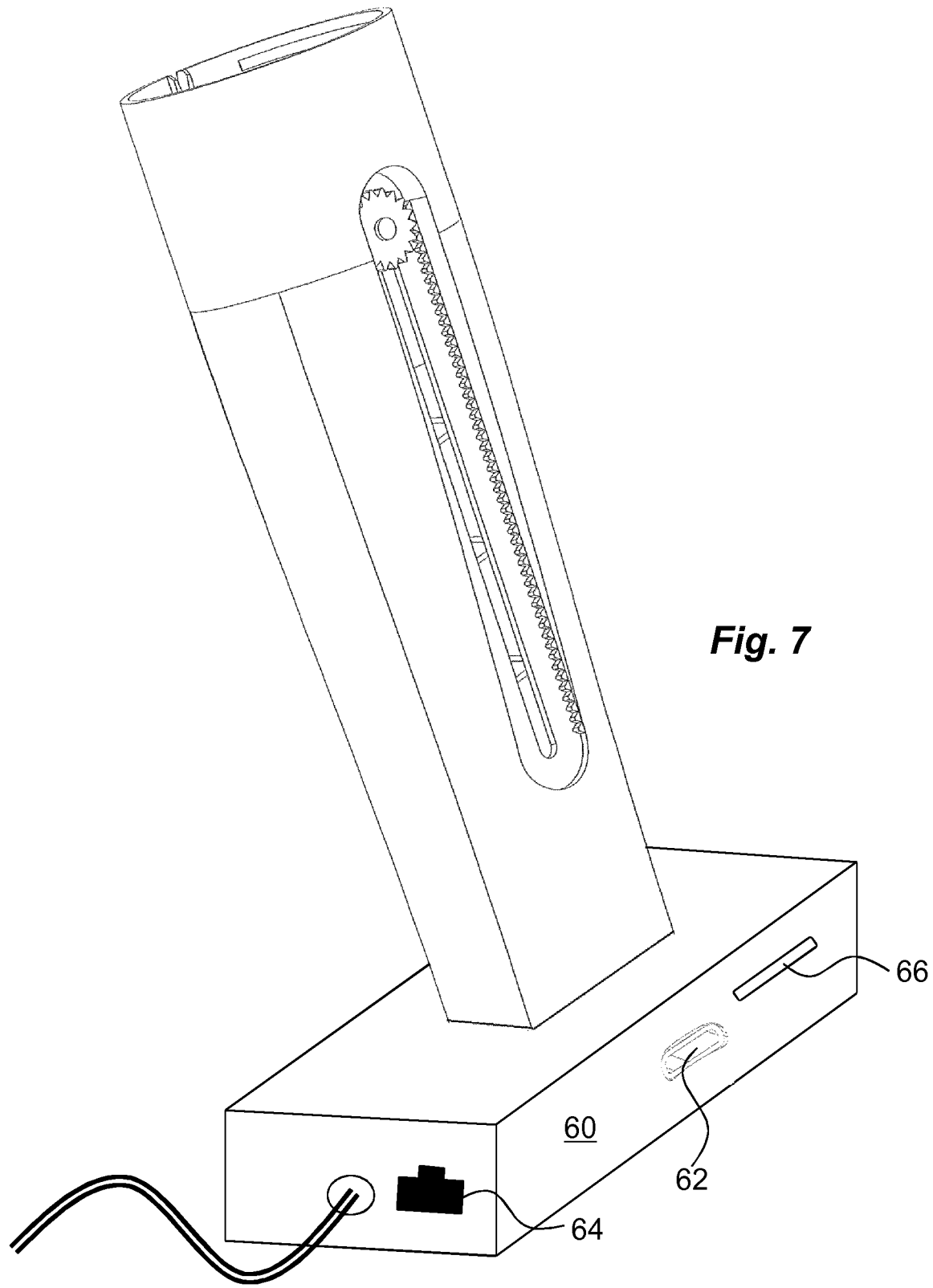
FIG. 7 shows a second embodiment of an information provider assembly.

If the medicament delivery device is not to be used very frequently, say for instance that the patient only needs to have an injection once per day or even once per week, the device may not be carried around but may instead be "stationary" in the home of the user. This in turn enables a modification of the information provider assembly. It does no longer have to be in the form of a slim protective cap but can instead be in the form of a stand 60 that can be placed for instance on a table as seen in FIG. 7. Since the requirements on size are no longer critical, it is possible to design the information provider assembly much more freely. For instance, the information provider assembly may be a stand as seen in FIG. 8.

This design provides the possibilities to incorporate functions and features into the stand. For instance, the stand can incorporate contacts such that information may be retrieved by external, connected devices, databases, information storage centres and the like. The contacts could e.g. be USB-ports 62, (standard, mini, micro), ethernet ports 64, or other types of I/O devices allowing external devices to be connected to the stand via suitable cables. The stand could also be arranged with a SIM-card reader 66 and a suitable GSM-circuit such that the device may communicate with external information receivers. In this case, the limitations with the portable cap can be omitted because of the larger volumes in the stand.

As an alternative to the rotary encoder, a linear encoder 70 could be used. In FIG. 8. A resistive path 72 is arranged on at least one side of the slit 42. The resistive path 72 is connected to a potentiometer circuit 76, which circuit is powered by a suitable power source such as a battery. A slider 78 is further attached to the collet 24 via a stand extending through the slit. As with the rotary encoder, the initial position when the collet 24 is in the most distal position is the starting position. As the collet 24 is moved in the proximal direction the slider 78 runs along the resistive path 72 providing a changing signal, where the signal corresponds to the length the collet 24 travels. When the collet stops, the resistive value is obtained by the potentiometer circuit 76 and stored in the electronics unit 52.

When the user now is to administer a dose of medicament, he/she removes the cap and sets a dose by moving the proximal housing part in relation to the distal housing part, such that the reference points are moved closer to each other. The user then administers a dose of medicament as described above. After use, the cap is re-connected to the proximal end of the medicament delivery device, alternatively the medicament delivery device is put back in the stand. Again the collet 24 is moved in the proximal direction to the new position dictated by the reference points 30, 56. The slider 78 moving along the resistive path 72 will provide a certain value at the new position, which value is obtained by the linear potentiometer circuit. The circuit then compares the initial value with the new value, where the difference constitutes the dose delivered.

It is to be understood that the embodiments described above and shown in the drawings are to be regarded only as non-limiting examples and that the invention may be modified in many ways within the scope of the patent claims.

The invention claimed is:

1. An information provider assembly comprising:
a housing configured to be releasably attachable to a medicament delivery device by moving a proximal part of the medicament delivery device into an open distal end of the housing; and
a measuring unit that, when the housing is attached to the medicament delivery device, is configured to detect:
a first position of the proximal part within the housing prior to the medicament delivery device being used to select a dose, and
a second position of the proximal part within the housing after the medicament delivery device has been used to select and administer the dose while the housing was unattached to the medicament delivery device,
wherein a distance between the first position and the second position is indicative of the dose,
wherein the measuring unit comprises a first contact surface configured to contact the proximal part when the housing is attached to the medicament delivery device.

2. The information provider assembly according to claim 1, wherein the measuring unit comprises a movable contact element that includes the first contact surface.

3. The information provider assembly according to claim 1, the housing comprising a second contact surface configured to contact a reference surface of the medicament delivery device when the housing is attached to the medicament delivery device, wherein the second contact surface is located at the open distal end of the housing.

4. The information provider assembly according to claim 1, further comprising a spring force element arranged to urge the measuring unit distally within the housing.

5. The information provider assembly according to claim 1, wherein the measuring unit comprises a rotary encoder operably arranged to rotate when the measuring unit is moved.

6. The information provider assembly according to claim 1, wherein the measuring unit comprises a linear encoder operably arranged to move linearly when the measuring unit is moved.

7. The information provider assembly according to claim 1, further comprising a communication unit operably arranged to communicate information obtained from the measuring unit to external information receivers.

8. The information provider assembly according to claim 1, wherein the information provider assembly is arranged as a cap configured to protect a proximal end of the medicament delivery device.

9. The information provider assembly according to claim 1, wherein the housing is configured to be placed over a proximal end of the medicament delivery device.

10. The information provider assembly according to claim 1, wherein the measuring unit comprises a cog wheel that is engaged with a toothed track of the housing.

11. The information provider assembly according to claim 1, the measuring unit comprising a collet, the information provider assembly further comprising a spring force element configured to urge the collet in a distal direction within the housing.

12. The information provider assembly according to claim 1, the measuring unit comprising a collet comprising an outwardly extending ridge that is configured to engage an inwardly extending guide ledge of the housing.

13. The information provider assembly according to claim 1, wherein the proximal part is in contact with a neck of a syringe of the medicament delivery device.

14. The information provider assembly according to claim 1, wherein the housing comprises a closed proximal end.

15. A medicament delivery system comprising the information provider assembly according to claim 1.

* * * * *